(12) United States Patent
Lee et al.

(10) Patent No.: US 9,411,155 B2
(45) Date of Patent: Aug. 9, 2016

(54) OPTICAL ZOOM PROBE

(71) Applicant: Samsung Electronics Co., Ltd., Suwon-si (KR)

(72) Inventors: Seung-wan Lee, Suwon-si (KR); Eun-sung Lee, Hwaseong-si (KR); Jong-hyeon Chang, Suwon-si (KR); Kyu-dong Jung, Suwon-si (KR); Min-seog Choi, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 288 days.

(21) Appl. No.: 14/040,851

(22) Filed: Sep. 30, 2013

(65) Prior Publication Data

US 2014/0092388 A1  Apr. 3, 2014

(30) Foreign Application Priority Data

Sep. 28, 2012 (KR) ........................ 10-2012-0109260

(51) Int. Cl.
| | |
|---|---|
| *G02B 26/10* | (2006.01) |
| *G02B 7/04* | (2006.01) |
| *A61B 1/00* | (2006.01) |
| *G02B 3/14* | (2006.01) |
| *A61B 5/00* | (2006.01) |
| *G01N 23/04* | (2006.01) |
| *G02B 23/24* | (2006.01) |
| *G01N 21/27* | (2006.01) |
| *G01N 21/17* | (2006.01) |

(52) U.S. Cl.
CPC ............. *G02B 26/10* (2013.01); *A61B 1/0019* (2013.01); *G02B 3/14* (2013.01); *G02B 7/04* (2013.01); *A61B 5/0066* (2013.01); *A61B 5/0068* (2013.01); *A61B 5/0073* (2013.01); *G01N 23/046* (2013.01); *G01N 2021/1787* (2013.01); *G01N 2223/419* (2013.01); *G02B 23/2438* (2013.01)

(58) Field of Classification Search
None
See application file for complete search history.

(56) References Cited

U.S. PATENT DOCUMENTS

| 7,978,346 | B1 | 7/2011 | Riza | |
|---|---|---|---|---|
| 8,184,367 | B2 | 5/2012 | Rolland et al. | |
| 2004/0254474 | A1* | 12/2004 | Seibel .................. | A61B 5/0062 600/473 |
| 2006/0256448 | A1* | 11/2006 | Oh ........................ | G02B 26/005 359/666 |
| 2007/0156021 | A1* | 7/2007 | Morse .................. | A61B 1/0019 600/167 |
| 2009/0147372 | A1* | 6/2009 | Chang ................ | G02B 13/0075 359/665 |
| 2010/0149651 | A1* | 6/2010 | Berge .................. | G02B 26/005 359/666 |
| 2010/0309560 | A1* | 12/2010 | Dharmatilleke ......... | G02B 3/14 359/666 |
| 2011/0118610 | A1* | 5/2011 | Kuiper ................. | A61B 1/0019 600/476 |
| 2012/0013990 | A1* | 1/2012 | Yamamoto ............... | G02B 3/14 359/666 |
| 2012/0026596 | A1* | 2/2012 | Berge .................. | G02B 26/005 359/665 |
| 2012/0143004 | A1* | 6/2012 | Gupta ................ | A61B 1/00096 600/117 |

(Continued)

FOREIGN PATENT DOCUMENTS

| EP | 1 798 958 A1 * | 6/2007 | ............. G02B 5/005 |
|---|---|---|---|
| JP | 201113582 A | 1/2011 | |

(Continued)

*Primary Examiner* — Gordon J Stock, Jr.
(74) *Attorney, Agent, or Firm* — Sughrue Mion, PLLC

(57) ABSTRACT

An optical zoom probe is provided. The optical zoom probe includes: an aperture adjuster which adjusts an aperture through which light which is transmitted by a light transmitter propagates; and a focus adjuster which focuses light that propagates through the aperture and which includes first and second liquid lenses for each of which respective curvatures are independently controlled so as to adjust a respective focal length.

19 Claims, 11 Drawing Sheets

(56) References Cited

U.S. PATENT DOCUMENTS

2013/0070249 A1 3/2013 Choi et al.
2013/0128368 A1* 5/2013 Costache ............ G02B 26/004
                                                359/666

FOREIGN PATENT DOCUMENTS

| KR | 1020120004457 A | 1/2012 |
| KR | 10-2013-0030104 A | 3/2013 |

* cited by examiner

OPTICAL ZOOM PROBE

CROSS-REFERENCE TO RELATED APPLICATION

This application claims priority from Korean Patent Application No. 10-2012-0109260, filed on Sep. 28, 2012, in the Korean Intellectual Property Office, the disclosure of which is incorporated herein by reference in its entirety.

BACKGROUND

1. Field

Exemplary embodiments relate to optical zoom probes, and more particularly, to optical zoom probes in which scanning may be performed both in a near distance and in the nearest distance.

2. Description of the Related Art

In the field of medical imaging, demands for performing tomography using information regarding the surface of a tissue (human body or skin) are increasing. In particular, because most types of cancers are generated in lower parts of epithelial cells and are propagated into dermal cells in which blood vessels exist, when cancer can be detected at an early stage, damage caused by cancer can be remarkably reduced. With respect to existing imaging techniques, such as magnetic resonance imaging (MRI), x-ray computed tomography (CT), and ultrasonic waves, although tomography can be performed on an inside of a tissue by penetrating the skin, early detection of cancer which involves a tumor having a small size cannot be performed due to low resolution. Conversely, because light is used in performing an optical coherence tomography (OCT) technique that has been recently introduced, unlike in the existing art, the depth of penetration into the skin is low, i.e., about 2 to 3 mm, and resolution is high, about 10 times better than the resolution of ultrasonic waves. Thus, the OCT technique is expected to be useful in diagnosing early stages of cancer which involve a tumor having the size of about 50 to 100 μm. However, because the resolution of the OCT technique is lower than that of a microscope, the OCT technique cannot replace biopsy and histology that are actually used for making conclusive determinations relating to cancer diagnoses.

Recently, some OCT researchers have conducted investigations relating to performing diagnosis of cancer inside a tissue in real-time by combining tomography characteristics of OCT and high-resolution surface photographing using a confocal microscope, for example, and without performing biopsy. However, an objective lens of the microscope requires an optical system with a high numerical aperture (NA) so as to realize a high resolution in a horizontal direction, whereas OCT requires an optical system which has relatively uniform spot sizes in a depth direction, i.e., having a large depth of focus (DOF) with a low NA.

SUMMARY

Provided are optical zoom probes in which high-resolution scanning may be performed while a focus is moved in the nearest distance mode and in a near distance mode.

Additional aspects will be set forth in part in the description which follows and, in part, will be apparent from the description, or may be learned by practice of the presented exemplary embodiments.

According to an aspect of one or more exemplary embodiments, an optical zoom probe includes: an aperture adjuster which adjusts an aperture through which light which is transmitted by a light transmitter propagates; and a focus adjuster which focuses light that propagates through the aperture and which includes a first liquid lens and a second liquid lens, for each of which respective curvatures are independently controllable so as to adjust a respective focal length.

The optical zoom probe may further include a third lens which has a positive power and which is arranged between the focus adjuster and an object.

The third lens may include an aspheric lens.

A transparent medium may be interposed between the first liquid lens and the second liquid lens, and the first liquid lens, the transparent medium, and the second liquid lens may be formed as a single body.

In a near scanning mode, each of the first and second liquid lenses may be caused to have a concave lens surface.

In a nearest scanning mode, at least one of the first and second liquid lenses may be caused to have a convex lens surface.

In the nearest scanning mode, one of the first and second liquid lenses that is closer to a scanning object may be caused to have a convex lens surface.

A protrusion variation quantity of each of the first and second liquid lenses may be equal to or less than 400 μm.

At least one of the first and second liquid lenses may further include a transparent film which has a curved surface, and in a near scanning mode, the curved surface of the transparent film may act as a lens surface, and in a nearest scanning mode, the curved surface of the transparent film may not act as the lens surface.

Each of the first and second liquid lenses may form a lens surface in conjunction with a surface of a fluid and may adjust the respective focal length by adjusting a respective shape of the lens surface by using a flow of the fluid.

The first and second liquid lenses may be configured such that the fluid flows in a first direction with respect to the first liquid lens, which first direction is opposite to a second direction with respect to the second liquid lens.

The flow of the fluid may occur according to an electrowetting principle.

At least one of the first and second liquid lenses may include: a first fluid that is transparent; a second fluid that does not mix with the first fluid and is transparent; a chamber having an internal space in which the first fluid and the second fluid are accommodated; a first surface that is a boundary surface between the first fluid and the second fluid and forms the lens surface; a second surface that is a boundary surface between the first fluid and the second fluid and induces a variation in a curvature of the lens surface; a first intermediate plate that is disposed in the chamber and has a first through hole which has a diameter that corresponds to the curvature of the lens surface and a second through hole that forms a passage of the second fluid; and an electrode which forms an electric field that causes a variation in a position of the second surface.

The first fluid may include a polar liquid, and the second fluid may include one from among a gas and a non-polar liquid.

The fluid may be caused to flow by using pressure.

At least one of the aperture adjuster and the focus adjuster may include a cover glass, and the cover glass may have a gradient which is less than or equal to about 12 degrees with respect to an optical axis.

The cover glass may be disposed on the aperture adjuster.

The cover glass may be disposed on at least one of an input terminal of the focus adjuster and an output terminal of the focus adjuster.

The optical zoom probe may further include at least one of: a first lens unit which collimates light which is transmitted by the light transmitter to be transmitted to the aperture adjuster; and a second lens unit which is disposed between the aperture adjuster and the focus adjuster.

The aperture adjuster may include a liquid iris diaphragm for which an aperture size is adjustable by using a microelectrofluidic method.

The aperture adjuster may include: a chamber forming a space in which a fluid flows; a first fluid and a second fluid that are disposed in the chamber and which do not mix with each other, wherein one of the first fluid and the second fluid is formed of a transparent material, and an other one of the first fluid and the second fluid is formed of one of a light-shielding material and a light-absorbing material; and an electrode unit which is disposed at an inside of the chamber and in which at least one electrode to which a voltage is applied, which voltage form an electric field in the chamber, is arranged, and wherein the aperture through which light propagates is adjustable based on a variation in a position of an interface between the first fluid and the second fluid based on the electric field.

One of the first fluid and the second fluid may include one of a liquid metal and a polar liquid, and an other one of the first fluid and the second fluid may include one of a gas and a non-polar liquid.

The light transmitter may include an optical fiber.

The optical fiber may have at least one characteristic from among a first characteristic of a gradient which is less than or equal to about 12 degrees with respect to an optical axis on an end of the optical fiber and a second characteristic of being anti-reflection coated.

According to another aspect of one or more exemplary embodiments, an image diagnosis system includes: a light source; the above-described optical zoom probe that irradiates light emitted from the light source onto an object; and a detector which detects an image of the object by using light reflected from the object.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
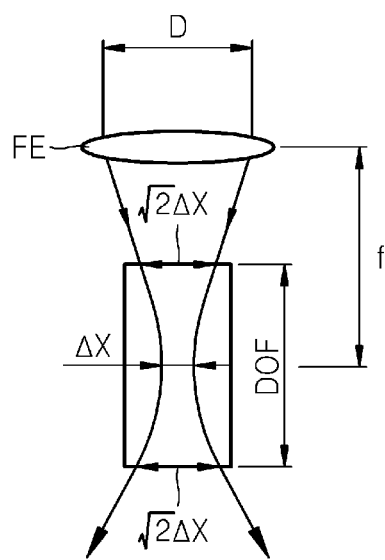
FIG. 1 is a conceptual view which illustrates a relationship between horizontal resolution and a depth of focus (DOF)

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present inventive concept will be described in detail by explaining exemplary embodiments with reference to the attached drawings. Like reference numerals in the drawings denote like elements. The sizes of elements in the drawings may be exaggerated for clarity and convenience.

FIG. 1 is a conceptual view which illustrates a relationship between horizontal resolution and a depth of focus (DOF).

A Gaussian beam is not a point, but instead has a beam waist which has a finite size $\Delta x$ when being focused, and $\Delta x$ is determined based on an aperture D and a focal length f by using Equation 1:

$$\Delta x = \frac{4}{\pi} \lambda \frac{f}{D} \tag{1}$$

$\Delta x$ is related to horizontal resolution. In particular, as $\Delta x$ decreases, horizontal resolution increases. As shown in Equation 1, because $\Delta x$ is proportional to f/D and a numerical aperture (NA) of a focusing lens FE is proportional to D/f, an optical system which has a relatively large value of NA is needed so that $\Delta x$ decreases, in order to obtain high horizontal resolution.

A depth of focus (DOF) is determined based on a beam diameter of $\sqrt{2}\Delta x$ by using Equation 2:

$$DOF = \frac{\pi}{2\lambda}(\Delta x)^2 \tag{2}$$

The DOF is a range within which the sizes of beam spots are relatively uniform in a depth direction. When image information which is based on a depth, such as, for example, an image of a tissue of the human body, is captured using tomography, an optical system is required to have a relatively large value of DOF, i.e., in order to have a correspondingly small value of NA.

In this way, horizontal resolution and the DOF have a trade-off relationship.

An optical zoom probe according to an exemplary embodiment may realize a horizontal resolution and a DOF that are required in order to scan an object with high resolution in a nearest distance mode and in a near distance mode. In particular, the "nearest distance" refers to a case for which a distance between a last lens of the optical zoom probe and an object, for example, the surface of a tissue, is equal to or less than about 2 mm, and the "near distance" refers to a case for which the distance between the last lens of the optical zoom probe to the object, for example, the surface of the tissue, is equal to or less than about 30 mm.

Figure 2:
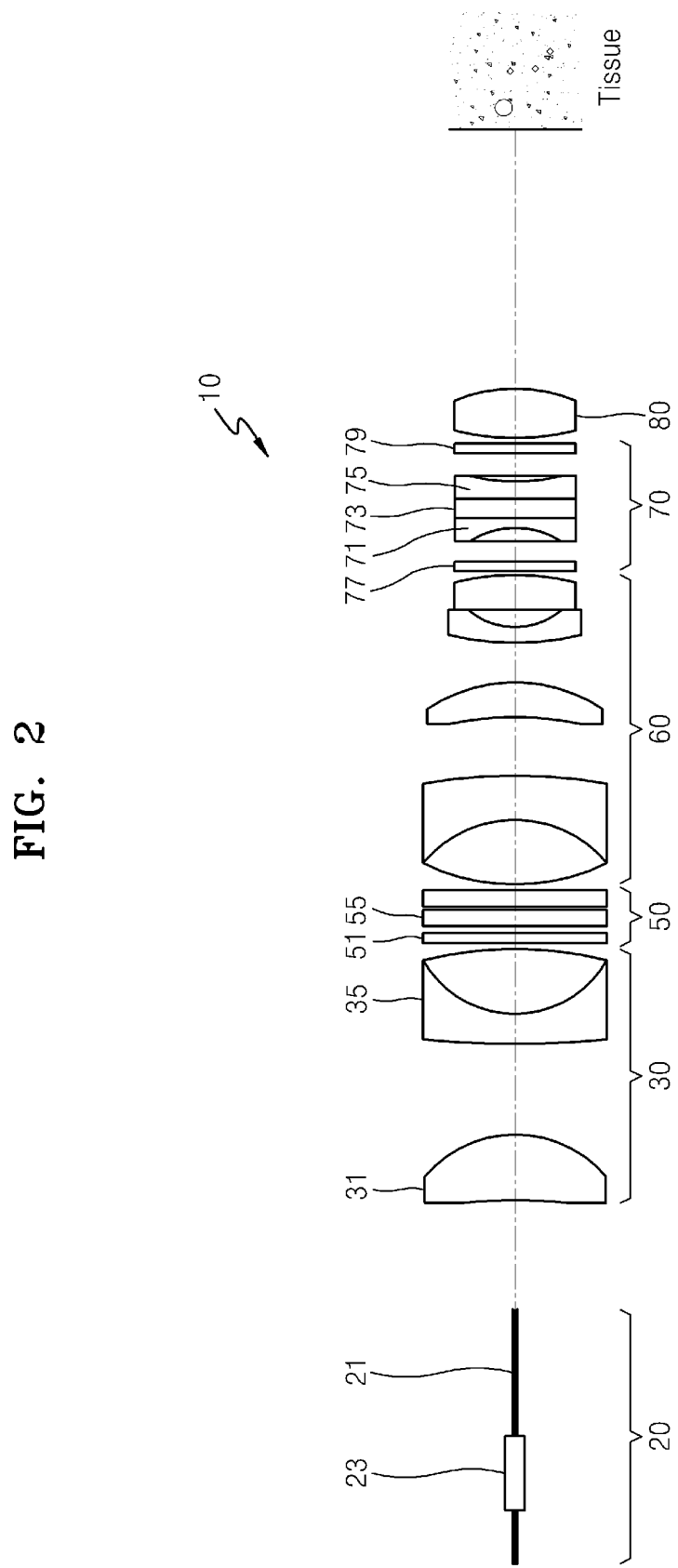
FIG. 2 is a view which schematically illustrates an overall optical configuration of an optical zoom probe, according to an exemplary embodiment.

FIG. 2 is a view which schematically illustrates an overall optical configuration of an optical zoom probe 10, according to an exemplary embodiment.

Referring to FIG. 2, the optical zoom probe 10 includes an aperture adjuster 50 that adjusts an aperture through which light which is transmitted through a light transmitter 20 propagates, and a focus adjuster 70 which includes a first liquid lens 71 and a second liquid lens 75, for each of which respective curvatures are independently adjustable. The optical zoom probe 10 may further include a third lens 80 which has a positive power in order to optimize a focus between the focus adjuster 70 and an object, for example, a tissue to be inspected. The third lens 80 may be, for example, an aspheric lens. The optical zoom probe 10 may further include at least one of a first lens unit 30 that collimates light transmitted by the light transmitter 20 to be transmitted to the aperture adjuster 50 and a second lens unit 60 that is disposed between the aperture adjuster 50 and the focus adjuster 70. FIG. 2 and the remaining drawings illustrate exemplarily that the optical zoom probe 10 includes both of the first lens unit 30 and the second lens unit 60. Hereinafter, the optical zoom probe 10 shall be described based on an optical system of FIG. 2, aspects of the present inventive concept are not limited thereto, and various modifications and equivalent embodiments thereof are possible.

The light transmitter 20 may further include an optical fiber 21 and a scanner 23 that is disposed on an end of the optical fiber 21. The scanner 23 is an actuator that induces deformation of the optical fiber 21 in order to change a path of light, such as, for example, a piezoelectric actuator or a cantilever which uses a piezoelectric body or a shape memory alloy. In addition, the scanner 23 may be formed using one or more of various materials in any of various ways.

The optical fiber 21 may have a gradient which is less than or equal to about 12 degrees with respect to an optical axis on its end, or may be anti-reflection coated on its end, or may have two composite characteristics such that noise which is caused by reflective light on the end of the optical fiber 21 to be scanned may be removed.

The first lens unit 30 collimates light which is transmitted by the light transmitter 20 such that light incident on the aperture adjuster 50 may be parallel light or approximately parallel light. The first lens unit 30 may include at least one of lenses 31 and 35. FIG. 2 and the following drawings illustrate exemplarily that the first lens unit 30 includes a single lens 31 and a doublet lens 35 that is spaced apart from the single lens 31 by a predetermined distance. This is just for illustrative purposes, and a lens configuration of the first lens unit 30 may be modified in various ways.

The aperture adjuster 50 adjusts the size of a light beam which is incident on the focus adjuster 70 in order to change the NA of the focus adjuster 70. For example, in an optical coherence microscopy (OCM) mode in which uniform high resolution is required in a section of about 2 mm in a depth direction in the relatively nearest scanning distance of about 2 mm or less, the aperture adjuster 50 increases the size of the light beam which is incident on the focus adjuster 70 so as to obtain a relatively high NA. In addition, in an optical coherence tomography (OCT) mode in which uniform spot sizes are required in a section of about 2 mm in the depth direction in the near scanning distance of between about 2 mm and 30 mm, the aperture adjuster 50 decreases the size of the light beam which is incident on the focus adjuster 70 so as to obtain a relatively low NA.

The aperture adjuster 50 may be, for example, a liquid iris diaphragm for which an aperture size is adjustable by using a microelectrofluidic method. In addition, the aperture adjuster 50 may be, for example, an iris diaphragm for which an aperture size is mechanically adjustable, or may be a liquid iris diaphragm for which an aperture size is adjustable by using a hydraulic pressure generated by a pump.

Figure 3:
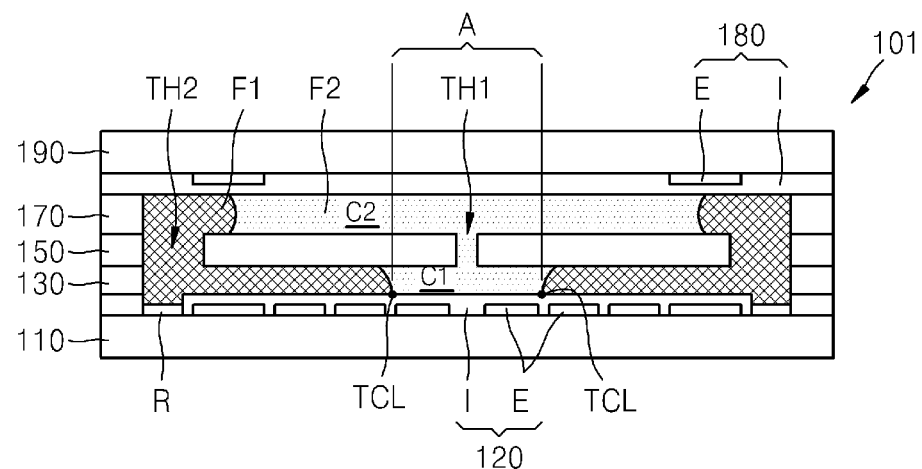
FIG. 3 illustrates an example of an aperture adjuster that may be used in the optical zoom probe illustrated in FIG. 2.
Figure 4:
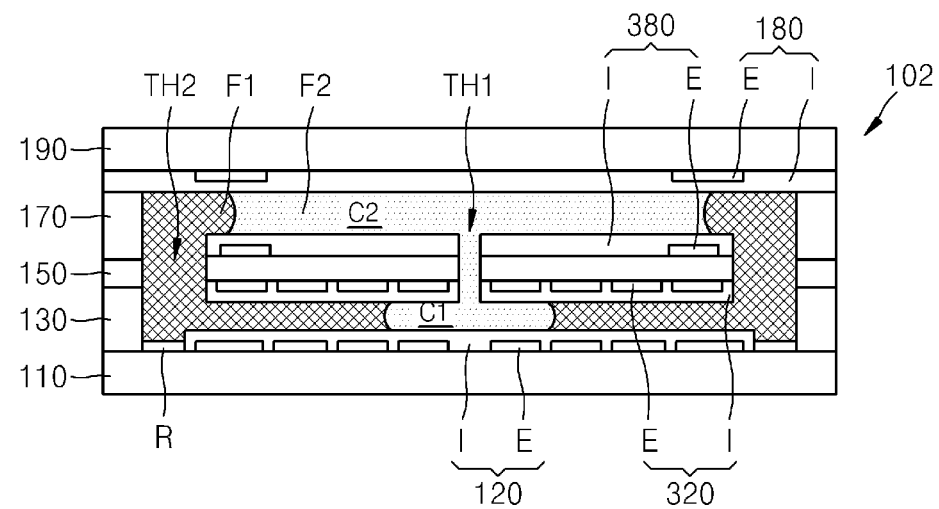
FIG. 4 illustrates another example of an aperture adjuster that may be used in the optical zoom probe of FIG. 2.

The aperture adjuster 50 may be an aperture adjuster 101 or 102 as illustrated in FIG. 3 or 4, for example.

FIG. 3 illustrates an example of the aperture adjuster 101 that may be used in the optical zoom probe 10 illustrated in FIG. 2.

Referring to FIG. 3, the aperture adjuster 101 may be configured so that a fluid may flow according to an electrowetting principle, and the size of an aperture A through which light propagates may be adjusted according to the flow of the fluid. The aperture adjuster 101 includes a chamber that forms a space in which the fluid flows, a first fluid F1 and a second fluid F2 that are accommodated in the chamber and that do not mix with each other, wherein one of the first fluid F1 and the second fluid F2 is formed of a transparent material and the other one is formed of one of a light-shielding material and a light-absorbing material, and an electrode unit which is disposed at an inside of the chamber and in which at least one electrode to which a voltage is applied, which voltage forms an electric field in the chamber, is arranged. The aperture A through which light propagates is adjusted based on a variation in the position of an interface between the first fluid F1 and the second fluid F2 based on the electric field.

For example, an area of the chamber includes a first channel C1 and a second channel C2 that is disposed above the first channel C1 and is connected to the first channel C1. The range of the aperture A may be determined based on a variation in the position of the interface between the first fluid F1 and the second fluid F2 that occurs in each of the first channel C1 and the second channel C2. The first channel C1 may be formed by a first substrate 110, a second substrate 150 that is spaced apart from the first substrate 110 by a predetermined distance, and a first spacer 130 that forms an internal space between the first substrate 110 and the second substrate 150. In this case, a first through hole TH1 may be formed in the center of the second substrate 150, and a second through hole TH2 may be formed on the periphery of the second substrate 150. In addition, the second channel C2 may be formed by the second substrate 150, a third substrate 190 that is spaced apart from the second substrate 150 by a predetermined distance, and a second spacer 170 that forms an internal space between the second substrate 150 and the third substrate 190.

One of the first fluid F1 and the second fluid F2 may be one of a liquid metal and a polar liquid, and the other one thereof may be one of a gas and a non-polar liquid.

The electrode unit may include a first electrode unit 120 that is formed on the first substrate 110 and includes at least one electrode E which is coated with an insulating material I, and a second electrode unit 180 that is formed on the third substrate 190 and includes at least one electrode E which is coated with the insulating material I.

The first electrode unit 120 may include a plurality of electrodes which are configured to digitally control the aperture A.

A ground electrode unit R may be disposed to maintain contact with a polar fluid in one or more portions inside the chamber. For example, the ground electrode unit R may be disposed to maintain contact with the polar first fluid F1. To this end, as illustrated in FIG. 3, the ground electrode unit R may be disposed on the first substrate 110, and the position of the ground electrode unit R may be changed.

At least one electrode E that is a constituent of each of the first electrode unit 120 and the second electrode unit 180 may be formed of a transparent conductive material. For example, at least one electrode E may be formed of a metal oxide, such as indium tin oxide (ITO) or indium zinc oxide (IZO); a metal nanoparticle dispersion thin layer, such as gold (Au) or silver (Ag); a carbon nanostructure, such as carbon nanotube (CNT) or graphene; or a conductive polymer, such as poly(3,4-ethylenedioxythiophene) (PEDOT), polypyrrole (PPy), or poly (3-hexylthiophene) (P3HT).

Because the ground electrode unit R does not require transparency in relation of a position, the ground electrode unit R may be formed of a metal thin layer, such as Au, Ag, aluminum (Al), chromium (Cr), or titanium (Ti).

An electrowetting phenomenon refers to the case in which, when a voltage is applied to an electrolyte droplet on an electrode which is coated with an insulating material, an angle of contact between the electrode and the electrolyte droplet is varied. In particular, the contact angle varies based on each interfacial tension in a three-phase contact line (TCL) in which the fluid, the droplet, and the insulating material contact one another. When the electrowetting phenomenon is used, the flow of the fluid may be quickly and efficiently controlled by using a low voltage, and in addition, the fluid may be transferred and controlled.

When an appropriate voltage is applied to one electrode E of the first electrode unit 120, an electromechanical force may act in the TCL on an activated driving electrode, i.e., in a contact line where the first fluid F1, the second fluid F2, and the insulating material I contact one another, and the first fluid F1 may move toward the center of the second substrate 150 via the first channel C1 so that the aperture A may be reduced. In addition, when an appropriate voltage is applied to the second electrode unit 180, the first fluid F1 may move toward the center of the second substrate 150 via the second channel C2, and the TCL of the first channel C1 may be pushed out toward the edge so that the aperture A may be enlarged. When the first electrode unit 120 includes a plurality of electrodes E, the size of the aperture A may be digitally controlled by varying the activated electrode.

Referring back to FIG. 2, the aperture adjuster 50 may include a cover glass 51 that is disposed on at least one of an input terminal and an output terminal of the aperture adjuster 50. In FIG. 2, the aperture adjuster 50 includes the cover glass 51 that is disposed on the input terminal of the aperture adjuster 50. Reference numeral 55 of FIG. 2 represents a portion of the aperture adjuster 50 where the size of the aperture A is adjusted.

When the size of the aperture A is adjusted by the fluid that flows according to the electrowetting principle, as illustrated in FIGS. 3 and 4, the first substrate 110 or the third substrate 190 of the aperture adjuster 101 may be used as a cover glass, or the aperture adjuster 101 may include an additional cover glass.

FIG. 4 illustrates another example of the aperture adjuster 102 that may be used in the optical zoom probe 10 of FIG. 2.

The aperture adjuster 102 of FIG. 4 is different from the aperture adjuster 101 of FIG. 3 in that the aperture adjuster 102 of FIG. 4 further includes a third electrode unit 320 and a fourth electrode unit 380, each including at least one electrode E which is coated with the insulating material I, on both surfaces of the second substrate 150. The third electrode unit 320 may be used for increasing a driving force which is generated in the first channel C1 in addition to the driving force which is generated by the first electrode unit 120, and the fourth electrode unit 380 may be used for increasing a driving force which is generated in the second channel C2 in addition to the driving force which is generated by the second electrode unit 180. The number of electrodes that constitute the third electrode unit 320 and the fourth electrode unit 380 is not limited to the number of electrodes illustrated in FIG. 4 and may be modified in various ways. In addition, although the third electrode unit 320 and the fourth electrode unit 380 are disposed on both surfaces of the second substrate 150, this is just for illustrative purposes, and the third electrode unit 320 or the fourth electrode unit 380 may be disposed only one surface of the second substrate 150.

Referring back to FIG. 2, the second lens unit 60 is used to transmit light that propagates through the aperture adjuster 50 to the focus adjuster 70, and may include at least one lens.

The focus adjuster 70 may include the first and second liquid lenses 71 for each of which respective curvatures are independently controllable so as to focus on light that propagates through the aperture of the aperture adjuster 50 and to adjust a respective focal length.

A transparent medium 73 may be interposed between the first liquid lens 71 and the second liquid lens 75. The first liquid lens 71, the transparent medium 73, and the second liquid lens 75 may be formed as a single body in a state where the transparent medium 73 is interposed between the first liquid lens 71 and the second liquid lens and 75. In this case, the first and second liquid lenses 71 and 75 may be moved in opposite directions when a focus-adjusting operation is performed in a state where one transparent medium 73 is interposed between the first liquid lens 71 and the second liquid lens 75, so as to optimize the focus adjuster 70 in a lengthwise direction. In this regard, the protrusion variation quantity of the first and second liquid lenses 71 and 75 may not be greater than 400 μm so as to minimize a distance between the first and second liquid lenses 71 and 75 when the curvatures of the first and second liquid lenses 71 and 75 are adjusted.

Each of the first and second liquid lenses 71 and 75 may be disposed to form a respective lens surface in conjunction with a surface of the fluid and to adjust the corresponding focal length by adjusting the shape of the lens surface by using the flow of the fluid.

When x,y scanning is performed in a predetermined range in a depth direction in the nearest distance mode between a last lens (lens 80 in FIG. 2) of the optical zoom probe 10 and an object, for example, a tissue, at a nearest distance of about 2 mm or less, that is, in the OCM mode, at least one of the first and second liquid lenses 71 and 75 may be driven or caused to have a convex lens surface, as will be described below with reference to FIGS. 9A and 9B. In this case, when scanning is performed at a nearest distance, that is, in the OCM mode, a liquid lens of the first and second liquid lenses 71 and 75 that is closer to the tissue, i.e., the second liquid lens 75, may be driven to have the convex lens surface.

In addition, when x,y scanning is performed in a predetermined range in the depth direction in the near distance mode between the last lens (lens 80 in FIG. 2) of the optical zoom probe 10 and the object, for example, the tissue, for example, at a near distance of about 30 mm or less, that is, in the OCT mode, the first and second liquid lenses 71 and 75 may be driven or caused to have convex lens surfaces, as will be described below with reference to FIG. 10.

The first and second liquid lenses 71 and 75 may be disposed so that the flow of the fluid, for example, may occur according to the electrowetting principle.

Figure 5:
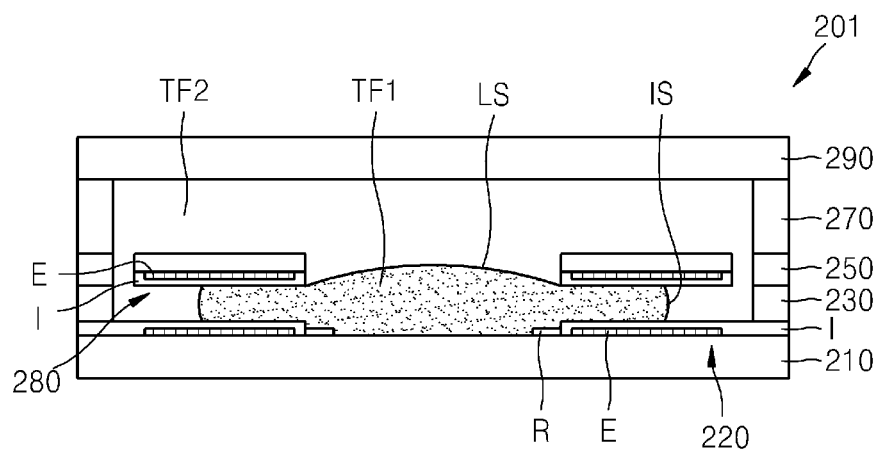
FIG. 5 illustrates an example of a liquid lens that may be used as a first liquid lens and/or a second liquid lens of a focus adjuster of the optical zoom probe of FIG. 2.

FIG. 5 illustrates an example of a liquid lens 201 that may be used as the first liquid lens 71 and/or the second liquid lens 75 of the focus adjuster 70 of the optical zoom probe 10 of FIG. 2.

Referring to FIG. 5, a first fluid TF1 that is transparent and polar and a second fluid TF2 that does not mix with the first fluid TF1 are accommodated in the chamber of the liquid lens 201. A boundary surface between the first fluid TF1 and the second fluid TF2 includes a first surface LS that forms a lens surface and a second surface IS that induces a variation in the curvature of the lens surface. In addition, an electrode unit which forms an electric field that causes a variation in the position of the second surface IS is formed in the chamber. A first intermediate plate 250, which has a first through hole TH1 that forms a diameter of a lens which corresponds to the lens surface and a second through hole TH2 that forms a path of the second fluid TF2, is disposed in the chamber so that the boundary surface between the first fluid TF1 and the second fluid TF2 may form the first surface LS that forms the lens surface and the second surface IS that induces a variation in the curvature of the lens surface.

A lower substrate 210 and an upper substrate 290 may be respectively disposed below and above the first intermediate plate 250, and a spacer unit may be formed between the lower substrate 210 and the first intermediate plate 250 and between the first intermediate plate 250 and the upper substrate 290 so as to form an internal space in the chamber. The spacer unit may include a first spacer 230 which is arranged between the lower substrate 210 and the first intermediate plate 250 and a second spacer 270 which is arranged between the first intermediate plate 250 and the upper substrate 290.

Each of the lower substrate 210, the first intermediate plate 250, and the upper substrate 290 may be formed of a transparent material.

The first fluid TF1 and the second fluid TF2 may be transparent fluids having different refractive indices. In this regard, the first fluid TF1 may be a polar liquid, and the second fluid TF2 may be one of a gas and a non-polar liquid.

Figure 6:
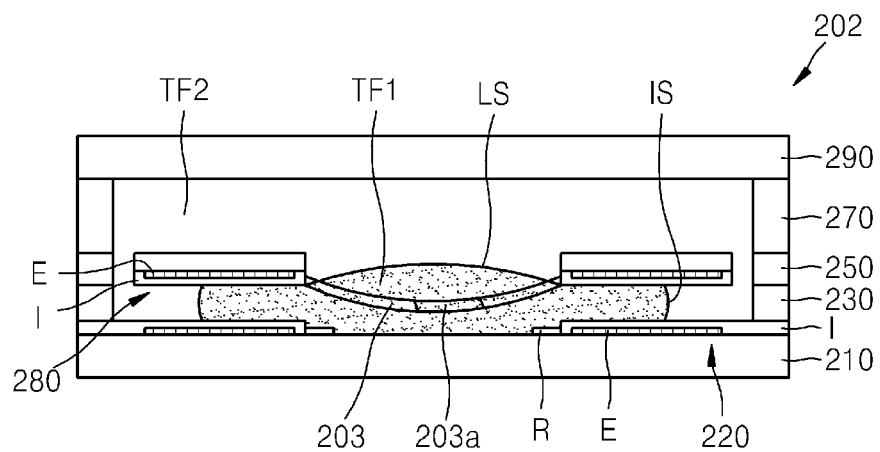
FIG. 6 illustrates another example of a liquid lens that may be used in a first liquid lens and/or a second liquid lens of the focus adjuster of the optical zoom probe of FIG. 2.

The electrode unit includes a first electrode unit 220 that is formed on a top surface of the lower substrate 210 and includes at least one electrode E for which a surface thereof is coated with the insulating material I, and a second electrode unit 280 that is formed on a bottom surface of the first intermediate plate 250 and includes at least one electrode E for which a surface thereof is coated with the insulating material I, as illustrated in FIG. 6. In an exemplary embodiment, only one of the first electrode unit 220 and the second electrode unit 280 may be disposed.

In addition, the electrode unit may further include a ground electrode R that contacts the first fluid TF1. Although the ground electrode R is illustrated as being disposed on the first substrate 210 in each of FIG. 5 and FIG. 6, the ground electrode R may be located in a position where the ground electrode R may contact the first fluid TF1 in a state where a voltage is not applied. The ground electrode R may be optional, and when the ground electrode R is disposed, a driving voltage may be reduced.

At least one electrode E that constitutes the first electrode unit 220 and the second electrode unit 280 may be formed of a transparent conductive material. For example, at least one electrode E may be formed of metal oxide, such as ITO or IZO, a dispersion thin film of metal nanoparticle such as Au or Ag, a carbon nanostructure, such as carbon nanotube (CNT) or grapheme, or a conductive polymer, such as poly(3,4-ethylenedioxythiophene)(PEDOT), polypyrrole (PPy), or poly(3-hexylthiophene) (P3HT). The ground electrode R may be formed of any one or more of the above-described transparent conductive materials, and when the ground electrode R does not require transparency based on its position, the ground electrode R may be formed of a thin film of metal such as Au, Ag, Al, Cr, or Ti.

In the liquid lens 201, the pressure that is exerted onto the second surface IS varies due to electrowetting driving and thus, the curvature of the first surface LS that is the lens surface is adjusted based on the pressure. When no voltage is applied to the electrode E or when the magnitude of the applied voltage is decreased, the second surface IS may be moved toward the center of the liquid lens 201, and the first surface LS that is the lens surface may become more convex. If the magnitude of the applied voltage is increased, the second surface IS may be moved toward both sides of the liquid lens 201, and the curvature of the first surface LS is decreased, and when the magnitude of the applied voltage is at a maximum, the first surface LS may have a concave curvature.

In FIG. 5, each of the first electrode unit 220 and the second electrode unit 280 includes one electrode E, and the position of the second surface IS varies by adjusting the magnitude of the voltage which is applied to the electrode E.

In particular, either or both of the first electrode unit 220 and the second electrode unit 280 may include a plurality of electrodes E which are coated with the insulating material I. In this regard, a voltage is applied to at least one of the electrodes E that constitute the first electrode unit 220 and the second electrode unit 280 so that the curvature of the first surface LS that is the lens surface may be digitally controlled. More particularly, when an appropriate voltage is applied to one electrode which is selected from the electrodes E, an electromechanical force is exerted on a TCL of the activated driving electrode, i.e., on a line where the second surface IS that is a boundary surface between the first fluid F1 and the second fluid F2 and the insulating material contact each other, and the position of the second surface IS is formed, and the curvature of the first surface LS may be determined based on the position of the second surface IS. When an appropriate voltage is applied to the electrode E that is disposed in the innermost portion of the electrode unit, the second surface IS may be moved toward the center of the liquid lens 201 to the utmost so that the curvature of the first surface LS may be increased. In addition, when an appropriate voltage is applied to the electrode E that is disposed in the outermost portion of the electrode unit, the second surface IS may be moved to both sides of the liquid lens 201 to the utmost, and the curvature of the second surface LS may be increased or concave.

FIG. 6 illustrates another example of a liquid lens 202 that may be used in the first liquid lens 71 and/or the second liquid lens 75 of the focus adjuster 70 of the optical zoom probe 10 of FIG. 2.

Referring to FIG. 6, the liquid lens 202 may include a transparent film 203 which has a lens shape and which is disposed between liquids so that a lens surface for which shape control is not necessary in the z-axis direction due to a long focal length of about 30 mm or a lens surface for which shape deformation is minimized may be the transparent film 203. The liquid lens 202 of FIG. 6 is different from the liquid lens 201 of FIG. 5 in that the liquid lens 202 of FIG. 6 further includes the transparent film 203 which has a curved surface. The curved surface of the transparent film 203 may be concave.

In this case, for example, in a near scanning mode, the first fluid TF1 and the second fluid TF2 are moved so that the first surface LS corresponds to the curved surface of the transparent film 203. Thus, the curved surface of the transparent film 203 may serve as a concave lens surface. In the nearest scanning mode, the first surface LS is positioned above the transparent film 203 so that the curved surface of the transparent film 203 may not serve as the lens surface. A through hole 203a may be formed in the transparent film 203 so that the first fluid TF1 and/or the second fluid TF2 may be moved. In FIG. 6, the first fluid TF1 is positioned on the transparent film 203 so that a convex boundary surface between the first fluid TF1 and the second fluid TF2 serves as the lens surface. If the first fluid TF1 203 is discharged to a lower part of the transparent film 203, the concave curved surface of the transparent film 203 serves as a concave lens surface.

Even in this case, in the liquid lens 202, the pressure that is exerted onto the second surface IS varies due to electrowetting driving. Thus, the curvature of the first surface LS that is the lens surface is adjustable based on the pressure.

In FIGS. 5 and 6, each of the first electrode unit 220 and the second electrode unit 280 includes one electrode E, and the position of the second surface IS varies by adjusting the magnitude of the voltage applied to the electrode E. Each of the first electrode unit 220 and the second electrode unit 280 may include a plurality of electrodes E that are coated with the insulating material I. In this case, a voltage is applied to at least one of the electrodes E that constitute the first electrode unit 220 and the second electrode unit 280 so that the curvature of the first surface LS that is the lens surface may be digitally controlled.

Figure 7:
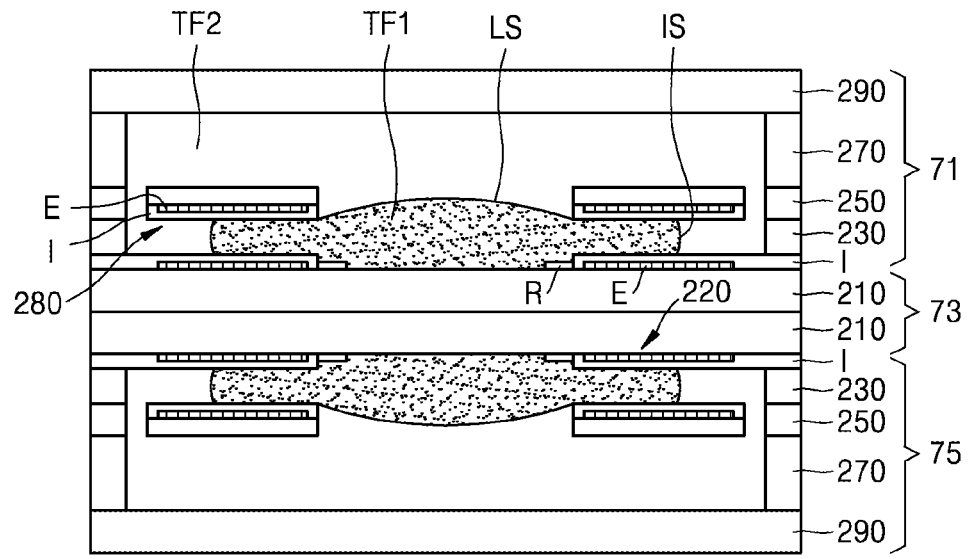
FIG. 7 illustrates an example in which a focus adjuster is configured to include first and second liquid lenses by combining liquid lenses of FIG. 5 with each other symmetrically.

FIG. 7 illustrates an example in which the focus adjuster 70 is configured to include the first and second liquid lenses 71 and 75 by combining the liquid lenses 201 of FIG. 5 with each other symmetrically. The focus adjuster 70, including the first and second liquid lenses 71 and 75, may have a structure in which the liquid lenses 202 of FIG. 6 are combined with each other symmetrically. In this case, the curvatures of the first liquid lens 71 and the second liquid lens 75 may be adjusted while being independently controlled.

In this case, the transparent medium 73 that is interposed between the first liquid lens 71 and the second liquid lens 75 may correspond to the lower substrate 210, and an additional transparent medium may be further interposed between the first liquid lens 71 and the second liquid lens 75. In FIG. 7, two lower substrates 210 are combined with each other by combining a pair of liquid lenses. The focus adjuster 70 may be configured so that only one lower substrate 210 may be disposed between the first liquid lens 71 and the second liquid lens 75.

Referring back to FIG. 2, the focus adjuster 70 may include cover glasses 77 and 79 that are disposed on at least one of an input terminal and an output terminal of the focus adjuster 70. FIG. 2 illustrates exemplarily that the cover glasses 77 and 79 are disposed on the input terminal and the output terminal of the focus adjuster 70, respectively.

When the focus adjuster 70 is configured to include the first and second liquid lenses 71 and 75 by combining two liquid lenses with each other symmetrically, as illustrated in FIG. 7, upper substrates 290 that are disposed in upper and lower portions of the focus adjuster 70 may be used as cover glasses, or additional cover glasses may be provided.

As described above, the first and second liquid lenses 71 and 75 of the focus adjuster 70 are disposed in such a way that the flow of the fluid occurs according to the electrowetting principle. However, aspects of the present inventive concept are not limited thereto. At least one of the first and second liquid lenses 71 and 75 may be a liquid lens 205 in which the flow of the fluid is caused by using pressure, as illustrated in FIG. 8.

Figure 8:
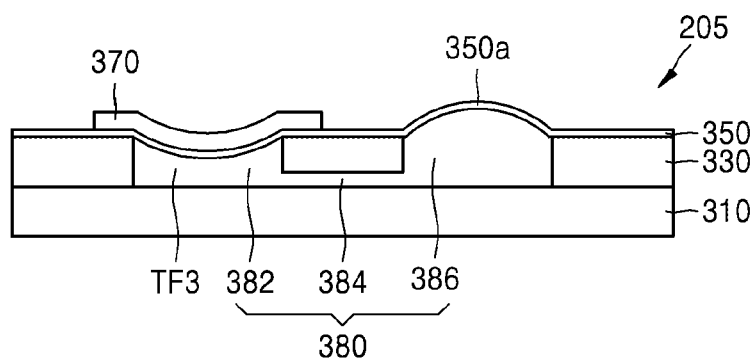
FIG. 8 illustrates another example of a liquid lens that may be used as a first liquid lens or a second liquid lens of the focus adjuster of the optical zoom probe of FIG. 2.

FIG. 8 illustrates another example of the liquid lens 205 that may be used as the first liquid lens 71 and/or the second liquid lens 75 of the focus adjuster 70 of the optical zoom probe 10 of FIG. 2.

Referring to FIG. 8, the liquid lens 205 may be configured in such a way that the flow of the fluid is caused by using pressure so as to vary the curvature of the lens surface. The liquid lens 205 includes a transparent fluid TF3 that is disposed in an internal space 380 of the chamber. The internal space 380 of the chamber is formed by a substrate 310 and a frame 330 which is formed on the substrate 310. The internal space 380 of the chamber may include a fluid chamber 382, a fluid path 384, and a lens chamber 386. A membrane 350 may be disposed on the frame 330, and an actuator 370 may be disposed on the membrane 350 that corresponds to an upper portion of the fluid chamber 382. One surface of the membrane 350 that corresponds to the upper portion of the lens chamber 386 may be a lens surface 350a.

The membrane 350 may be formed of a transparent and elastic material, such as, for example, silicon elastomer. In addition, polydimethylsiloxane (PDMS), which has high durability and flexibility, may be used in forming the membrane 350.

The actuator 370 may be used in applying pressure to the transparent fluid TF3 and may be a general actuator that uses any one or more of various methods. For example, the actuator 370 may be a general polymer actuator which is formed of an electro active polymer (EAP) having a very thin thickness and low power consumption, such as, for example, a relaxor ferroelectric polymer actuator formed of copolymer, such as P(VDF-TrFE_CFE) or P(VDF-TrFE-CTFE). The actuator 370 is electrostrictively constrained as a voltage is applied to the actuator 370, so that the actuator 370 applies pressure to the adjacent transparent fluid TF3.

The transparent fluid TF3 may be silicon oil, for example.

When pressure is applied to the transparent fluid TF3 in the fluid chamber 382 as the actuator 370 is driven, the transparent fluid TF3 moves to the lens chamber 386 along the fluid path 384 so that the shape of the lens surface 350a varies.

The liquid lens that may be used as the first liquid lens 71 or the second liquid lens 75 of the focus adjuster 70 of the optical zoom probe 10 of FIG. 2 may have a different structure from the above-described structure; for example, the liquid lens may include a liquid crystal lens that adjusts a focal length by forming an electric field gradient on a liquid crystal and by inducing a refractive index gradient caused by the electric field gradient.

In the optical zoom probe 10 according to the exemplary embodiment as described above, the focal length varies based on respective adjustments of the curvatures of the first and second liquid lenses 71 and 75, and a resolution of the optical zoom probe 10 may be adjusted by adjusting the size of the aperture.

Figure 9A:
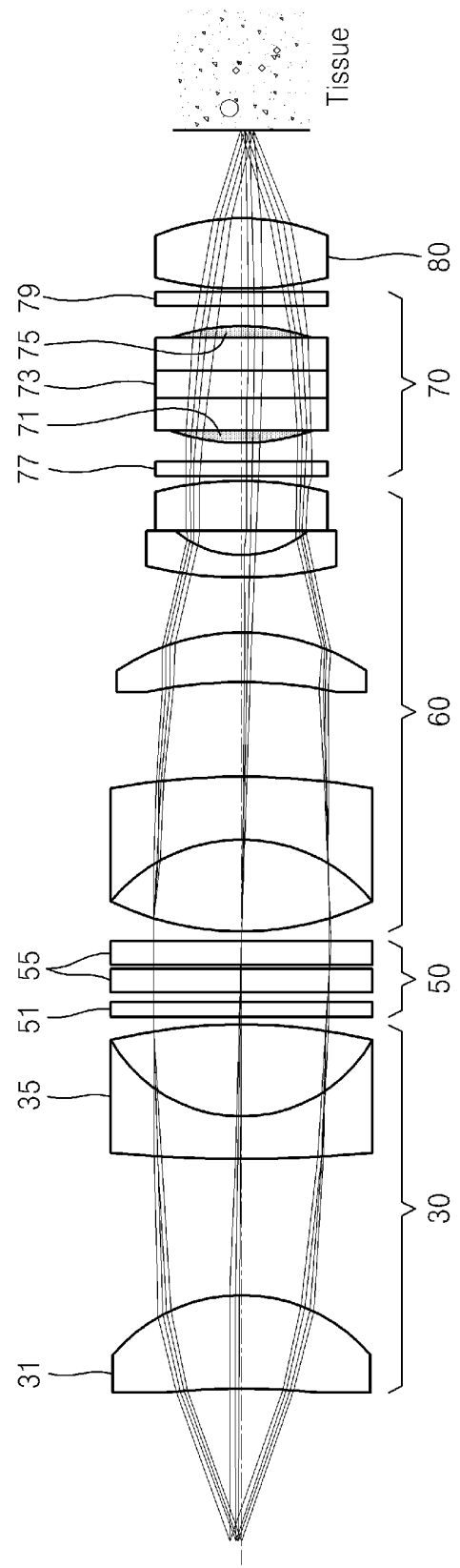
FIGS. 9A and 9B illustrate an operating state of the optical zoom probe of FIG. 2 when an object, for example, a tissue is scanned from a surface of the tissue to a relatively shallow depth.
Figure 9B:
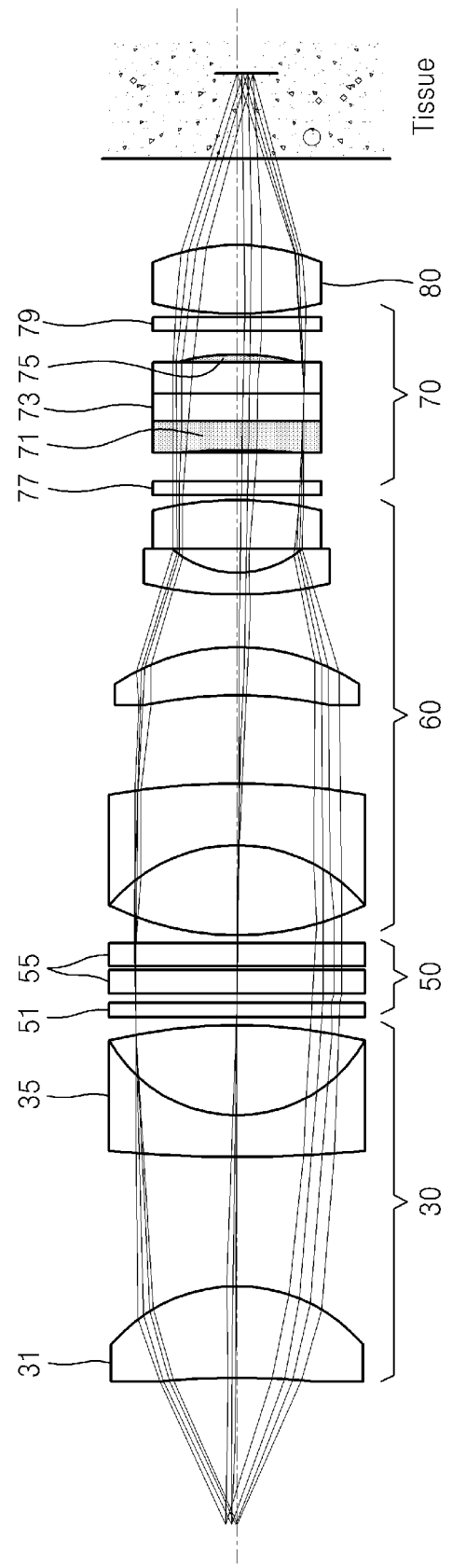
Figure 10:
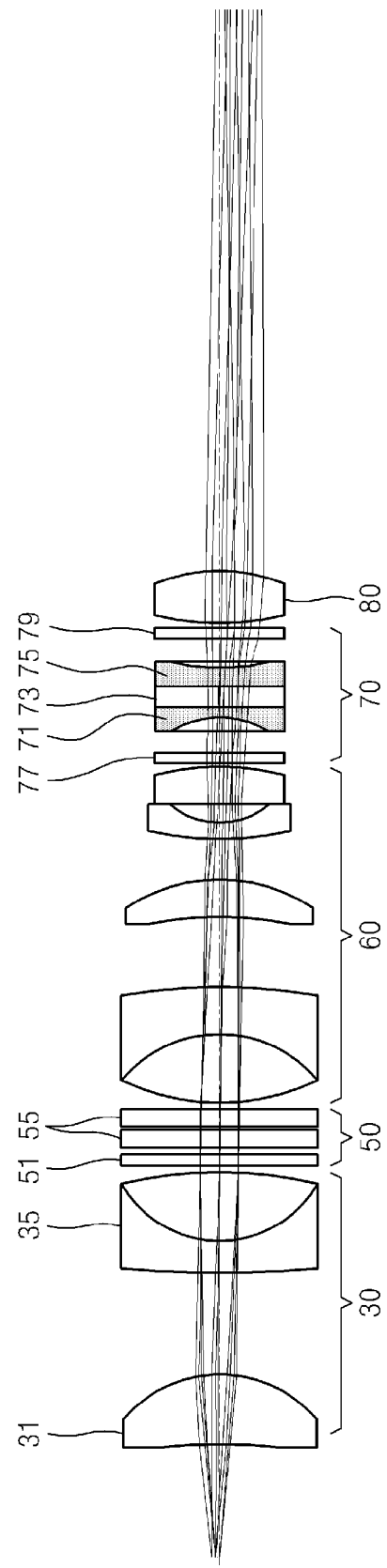
FIG. 10 illustrates an operating state of the optical zoom probe of FIG. 2 when scanning is performed with a long focal length.

FIGS. 9A and 9B and FIG. 10 illustrate a depth scanning method which may be performed by using the optical zoom probe 10 of FIG. 2. As illustrated in FIGS. 9A and 9B and FIG. 10, in the optical zoom probe 10 according to an exemplary embodiment, even though a depth of an object varies, scanning may be performed while maintaining a horizontal resolution of the optical zoom probe 10.

FIGS. 9A and 9B illustrate an operating state of the optical zoom probe 10 of FIG. 2 when an object, for example, a tissue of a body part, is scanned from a surface of the tissue to a relatively shallow depth, and FIG. 10 illustrates an operating state of the optical zoom probe 19 of FIG. 2 when scanning is performed with a long focal length.

As illustrated in FIG. 9A, when the size of the aperture of the aperture adjuster 50 is set to be appropriate and lens surfaces of the first liquid lens 71 and the second liquid lens 75 are convex curved surfaces, light is focused on the surface of an object, for example, a tissue of a body part, approximately in the nearest distance. In this case, a distance between the last lens 80 of the optical zoom probe 10 and the tissue may be less than or equal to about 2 mm, for example. In this case, when the path of light is changed by inducing deformation of the optical fiber 21 due to the scanner 23 of the light transmitter 20, the surface of the tissue may be scanned in a predetermined range of the x,y-plane.

As illustrated in FIG. 9B, when the size of the aperture of the aperture adjuster 50 is larger than in FIG. 9A, the lens surface of the first liquid lens 71 is slightly concave and the lens surface of the second liquid lens 75 that is relatively close to the tissue is convex, a horizontal resolution of light spots may be maintained, and the light spots are formed to a predetermined depth from the surface of the tissue. For example, the light spots may be formed to a depth of about 2 mm from the surface of the tissue. Even in this case, when the light spots are formed to a predetermined depth and a path of light is changed by inducing deformation of the optical fiber 21 due to the scanner 23 of the light transmitter 20, an inner side of the tissue may be scanned to a predetermined depth of the x,y-plane.

In this way, the optical zoom probe 10 according to the present exemplary embodiment may operate so that an OCM mode in which high-resolution scanning is performed in the nearest distance mode (i.e., a distance between the last lens and the surface of the tissue is less than or equal to about 2 mm) may be implemented. In particular, the tissue may be optically scanned with uniform resolution in a three-dimensional (3D) section of about 2 mm in a depth direction at a nearest distance which is less than or equal to about 2 mm.

As illustrated in FIG. 10, when the size of the aperture of the aperture adjuster 50 is smaller than in FIGS. 9A and 9B and the lens surfaces of the first liquid lens 71 and the second liquid lens 75 are concave, light may be focused in a relatively far distance from the last lens, for example, in a range of about 30 mm. In this case, a position in which the light spots are focused may vary based on an adjustment of the size of the aperture of the aperture adjuster 50 and respective curvatures of the concave curved surfaces of the first and second liquid lenses 71 and 75. Even in this case, when a path of light is changed by inducing deformation of the optical fiber 21 due to the scanner 23 of the light transmitter 20, scanning may be performed by changing a horizontal position in which the light spots are formed in a predetermined range of the x,y-plane.

As illustrated in FIG. 10, the optical zoom probe 10 according to the present exemplary embodiment may operate so that an OCT mode in which scanning may be performed in the near distance mode (i.e., a distance between the last lens and the surface of the tissue is less than or equal to about 30 mm), may be implemented. In particular, the tissue may be optically scanned with uniform resolution in a 3D section of about 2 mm in the depth direction at a near distance which is less than or equal to about 30 mm.

In this way, when the size of the aperture of the aperture adjuster 50 is adjusted, and simultaneously the directions of the curvatures and the curvatures of the lens surfaces of the first liquid lens 71 and the second liquid lens 72 are adjusted in order to adjust the focal length of the focus adjuster 70, the tissue may be optically scanned to a predetermined depth while maintaining a horizontal resolution as a high resolution.

When scanning is performed in the nearest distance mode, the second liquid lens 75 that is relatively close to the object may form a convex curved surface, and when scanning is performed in the near distance mode, both of the first and second liquid lenses 71 and 75 may form concave curved surfaces. However, aspects of the present inventive concept are not limited thereto, and various modifications and equivalent exemplary embodiments may be possible.

In the optical zoom probe 10 according to the present exemplary embodiment, an element which has a plane which is perpendicular to the path of light may be anti-reflection coated, and/or may have a predetermined gradient with respect to the optical axis so as to eliminate noise caused by reflective light.

Figure 11:
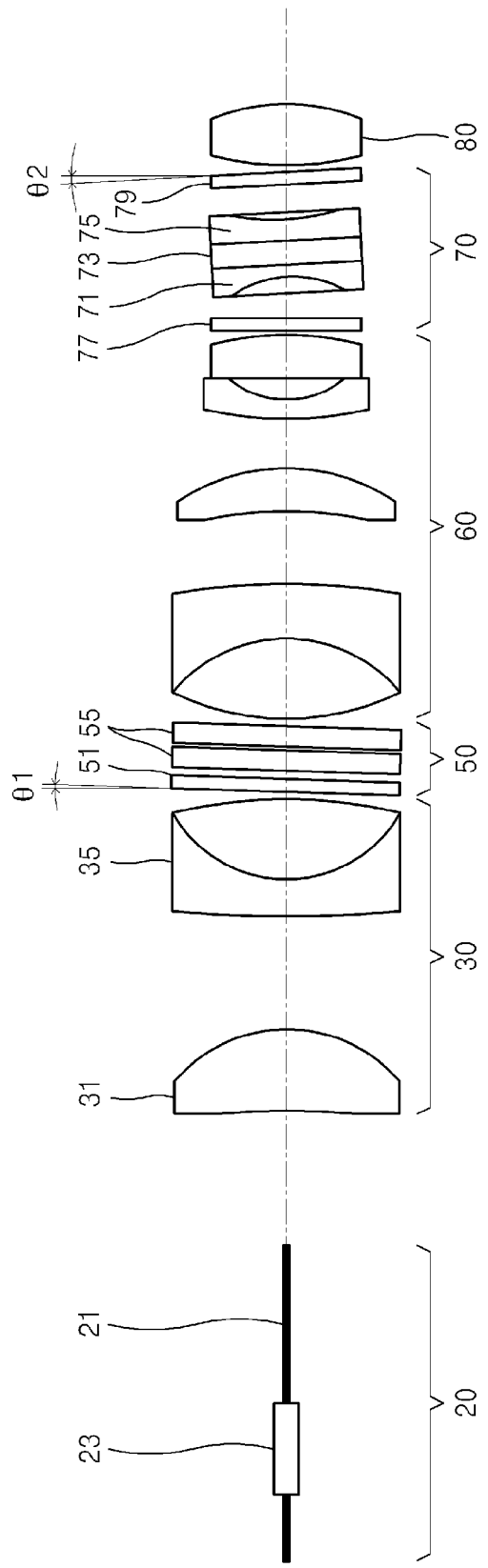
FIG. 11 is a view which schematically illustrates an overall optical configuration of an optical zoom probe according to another exemplary embodiment.

FIG. 11 is a view which schematically illustrates an overall optical configuration of an optical zoom probe, according to another exemplary embodiment.

For example, the cover glass 51 of the aperture adjuster 50 and/or the cover glasses 77 and 79 of the focus adjuster 70 may be arranged to be inclined at predetermined angles θ1 and/or θ2, as illustrated in FIG. 11. FIG. 11 illustrates exemplarily that both of the aperture adjuster 50 and the focus adjuster 70 are arranged to be inclined; however, in another exemplary embodiment, only one of the aperture adjuster 50 and the focus adjuster 70 may be arranged to be inclined.

In this regard, an inclination angle may be less than or equal to about 12 degrees. In particular, the cover glass 51 of the aperture adjuster 50 and/or the cover glasses 77 and 79 of the focus adjuster 70 may be arranged to have a gradient which is less than or equal to about 12 degrees with respect to an optical axis, for example, a gradient of about 4 degrees and a gradient of about 12 degrees with respect to the optical axis. For example, the cover glass 51 of the aperture adjuster 50 and/or the cover glasses 77 and 79 of the focus adjuster 70 may be arranged to have a gradient of about 8 degrees with respect to the optical axis.

Figure 12:
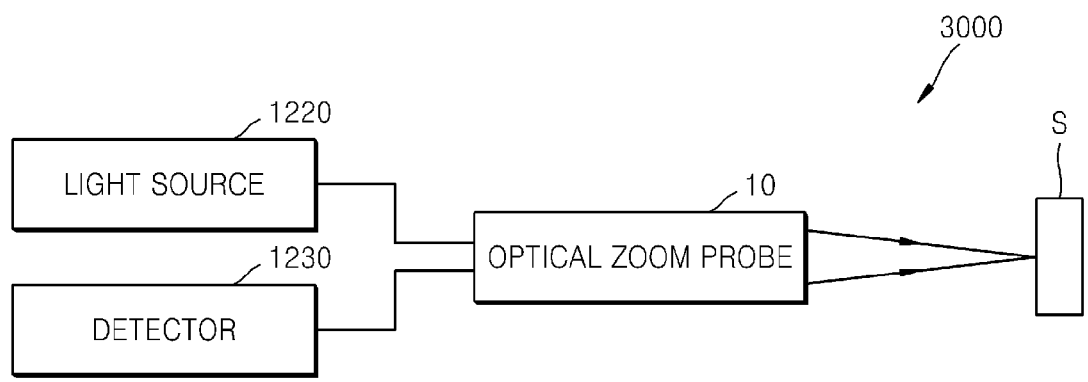
FIG. 12 is a schematic view of an image diagnosis system using the optical zoom probe, according to an exemplary embodiment.

FIG. 12 is a schematic view of an image diagnosis system 3000 which uses the optical zoom probe, according to an exemplary embodiment.

Referring to FIG. 12, the image diagnosis system 3000 includes a light source 1220, the optical zoom probe 10 that scans light which is emitted from the light source toward an object S, for example, a tissue to be inspected, and a detector 1230 that detects an image of the object by using light which is reflected from the object.

An optical zoom probe may be the optical zoom probe 10 according to the exemplary embodiment described above, and may properly adjust the size of the aperture, the focal length, and the like based on inspection purposes. The detector may include an image sensor, such as a charge-coupled device (CCD) that senses the image of the object.

In particular, the image diagnosis system 3000 may further include a beam splitter that splits the path of the light which is irradiated onto the object S from the light source 1220 and the path of the light which is reflected from the object S, and an image signal processor that processes signals sensed by the detector into image signals and displays the image signals.

The image diagnosis system 3000 may be configured to cause an interference between light reflected from the object and reference light by scanning the tissue to be inspected, by using the optical zoom probe 10, and to detect signal light. To this end, the optical zoom probe 10 may further include an optical system that splits light which is emitted from the light source 1220 that is the same as a light source from which the light is irradiated onto the object S so as to use one split light as the light irradiated onto the object S, to use another split light as the reference light, and that causes an interference between the light reflected from the object S and the reference light.

In this case, when the object S is scanned while moving the focal length in the nearest distance and in the near distance, in particular, when the conversion of the OCM mode and the OCT mode occurs, the length of the path of the light irradiated onto the object S varies, so that the length of the path of the reference light should be changed accordingly.

Figure 13:
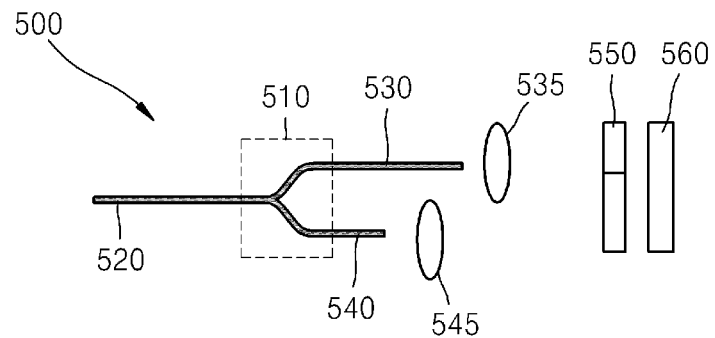
FIGS. 13, 14, and 15 are schematic views of various optical systems that may be used in adjusting the length of a path of reference light when an optical coherence microscopy (OCM) mode and an optical coherence tomography (OCT) mode are used, according to one or more exemplary embodiments.
Figure 14:
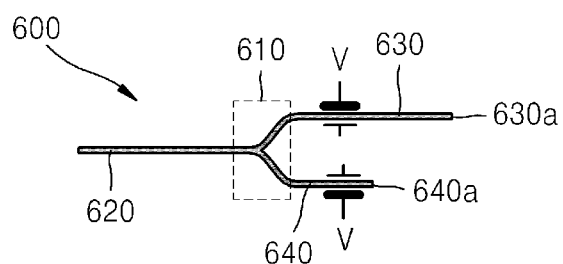
Figure 15:
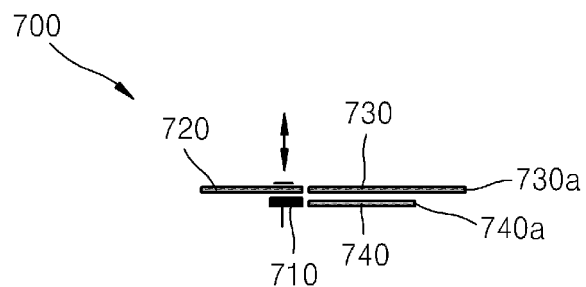

FIGS. 13, 14, and 15 15 are schematic views of various optical systems 500, 600, and 700 that may be used in adjusting the length of a path of reference light when an OCM mode and an OCT mode are used.

FIGS. 13 and 14 illustrate examples in which the reference light proceeds with optical fibers having different lengths according to the OCM or OCT mode by using couplers 510 and 610 of the respective optical systems 500 and 600.

Referring to FIG. 13, the coupler 510 is configured such that one end of the coupler 510 is connected to one optical fiber 520 and the other end thereof is connected to two optical fibers 530 and 540 which have different respective lengths. Collimating lenses 535 and 545 may be respectively disposed on input/output terminals of the optical fibers 530 and 540 so as to collimate the reference light which is respectively output from the optical fibers 530 and 540 and to focus the reference light which is reflected by a reflection mirror 560 to be respectively input to the optical fibers 530 and 540. A shutter 550 may be disposed between the optical fibers 530 and 540 and the reflection mirror 560.

For example, when the required length of the path of the reference light is relatively large, the shutter 550 may operate to pass the reference light which is output from the optical fiber 530, which has a relatively large length, through the shutter 550, and not to pass the reference light which is output from the optical fiber 540, which has a relatively small length, through the shutter 550. The reference light that is output from the optical fiber 530 and passes through the shutter 550 is reflected by the reflection mirror 560, passes through the shutter 550, and is input to the optical fiber 530.

Further, when the required length of the path of the reference light is relatively small, the shutter 550 may operate to pass the reference light which is output from the optical fiber 540, which has a relatively small length, through the shutter 550, and not to pass the reference light which is output from the optical fiber 530, which has a relatively large length, through the shutter 550. The reference light that is output from the optical fiber 540 and passes through the shutter 550 is reflected by the reflection mirror 560, passes through the shutter 550, and is input to the optical fiber 540.

Referring to FIG. 14, the coupler 610 is configured such that one end of the coupler 610 is connected to one optical fiber 620 and the other end thereof is connected to two optical fibers 630 and 640 which have different respective lengths. Input/output terminals 630a and 640a of the optical fibers 630 and 640 may be reflection coated using a reflection material, such as gold (Au) or silver (Ag), such that the reference lights which are output from the optical fibers 630 and 640 may be respective reflected on the input/output terminals 630a and 640a of the optical fibers 630 and 640 without any change, and the reflected reference light may proceed in opposite directions. Due to an external force which is generated when a voltage is applied to the coupler 610, light that proceeds via two optical fibers 630 and 640 having different lengths may be selectively cut.

FIG. 15 illustrates an example in which reference light from one-end optical fiber 720 proceeds via one of optical fibers 730 and 740, which have different respective lengths based on modes, by using an optical switch 710 of the optical system 700. Input/output terminals 730a and 740a of the optical fibers 730 and 740 may be reflection coated using a reflection material, such as gold (Au) or silver (Ag), such that the reference lights output from the optical fibers 730 and 740 may be reflected without any change, and the reflected reference light may proceed in opposite directions.

As described above, according to the one or more of the above exemplary embodiments, a focus adjuster includes a pair of liquid lenses that are independently controlled, and an aperture adjuster adjusts the size of an aperture so that an optical zoom probe in which high-resolution scanning may be performed while a focus is moved in the nearest distance and/or in a near distance, may be implemented.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

What is claimed is:

1. An optical zoom probe comprising:
   an aperture adjuster which adjusts an aperture through which light which is transmitted by a light transmitter propagates; and
   a focus adjuster which focuses light that propagates through the aperture and which comprises a first liquid lens and a second liquid lens, for each of which respective curvatures are independently controllable so as to adjust a respective focal length,
   wherein at least one of the first and second liquid lenses further comprises a transparent film which has a curved surface and within which a through hole is formable, and in a near scanning mode, the curved surface of the transparent film acts as a lens surface, and in a nearest scanning mode, the curved surface of the transparent film does not act as the lens surface.

2. The optical zoom probe of claim 1, wherein a transparent medium is interposed between the first liquid lens and the second liquid lens, and the first liquid lens, the transparent medium, and the second liquid lens are formed as a single body.

3. The optical zoom probe of claim 1, wherein, in the near scanning mode, each of the first and second liquid lenses is caused to have a concave lens surface.

4. The optical zoom probe of claim 1, wherein a protrusion variation quantity of each of the first and second liquid lenses is equal to or less than 400 μm.

5. The optical zoom probe of claim 1, further comprising at least one of:
   a first lens unit which collimates light transmitted by the light transmitter to be transmitted to the aperture adjuster; and
   a second lens unit which is disposed between the aperture adjuster and the focus adjuster.

6. The optical zoom probe of claim 1, wherein the light transmitter comprises an optical fiber, wherein the optical fiber has at least one characteristic from among a first characteristic of a gradient which is less than or equal to 12 degrees with respect to an optical axis on an end of the optical fiber and a second characteristic of being anti-reflection coated.

7. An image diagnosis system comprising:
a light source;
the optical zoom probe of claim 1 that irradiates light emitted from the light source onto an object; and
a detector which detects an image of the object by using light reflected from the object.

8. The optical zoom probe of claim 1, further comprising a third lens which has a positive power and which is arranged between the focus adjuster and an object to be scanned.

9. The optical zoom probe of claim 1, wherein, in the nearest scanning mode, at least one of the first and second liquid lenses is caused to have a convex lens surface.

10. The optical zoom probe of claim 1, wherein the aperture adjuster comprises a liquid iris diaphragm for which an aperture size is adjustable by using a microelectrofluidic method.

11. The optical zoom probe of claim 1, wherein each of the first and second liquid lenses forms a lens surface in conjunction with a surface of a fluid and adjusts the respective focal length by adjusting a respective shape of the lens surface by using a flow of the fluid.

12. The optical zoom probe of claim 1, wherein at least one of the aperture adjuster and the focus adjuster comprises a cover glass, and the cover glass has a gradient which is less than or equal to 12 degrees with respect to an optical axis.

13. The optical zoom probe of claim 8, wherein the third lens comprises an aspheric lens.

14. The optical zoom probe of claim 9, wherein, in the nearest scanning mode, one of the first and second liquid lenses that is closer to an object to be scanned is caused to have a convex lens surface.

15. The optical zoom probe of claim 10, wherein the aperture adjuster comprises:
a chamber forming a space in which a fluid flows;
a first fluid and a second fluid that are disposed in the chamber and which do not mix with each other, wherein one of the first fluid and the second fluid is formed of a transparent material, and an other one of the first fluid and the second fluid is formed of one of a light-shielding material and a light-absorbing material; and
an electrode unit which is disposed at an inside of the chamber and in which at least one electrode to which a voltage is applied, which voltage forms an electric field in the chamber, is arranged, and
wherein the aperture through which light propagates is adjustable based on a variation in a position of an interface between the first fluid and the second fluid based on the electric field.

16. The optical zoom probe of claim 11, wherein the first and second liquid lenses are configured such that the fluid flows in a first direction with respect to the first liquid lens, which first direction is opposite to a second direction with respect to the second liquid lens.

17. The optical zoom probe of claim 11, wherein the flow of the fluid occurs according to an electrowetting principle or pressure principle.

18. The optical zoom probe of claim 12, wherein the cover glass is disposed on the aperture adjuster.

19. The optical zoom probe of claim 12, wherein the cover glass is disposed on at least one of an input terminal of the focus adjuster and an output terminal of the focus adjuster.

* * * * *